United States Patent
Lichenstein et al.

(10) Patent No.: US 10,729,694 B2
(45) Date of Patent: Aug. 4, 2020

(54) ANTI-VIRAL COMPOSITIONS CONTAINING PIKFYVE INHIBITORS AND USE THEREOF

(71) Applicant: AI Therapeutics, Inc., Guilford, CT (US)

(72) Inventors: Henri Lichenstein, Guilford, CT (US); Jonathan M. Rothberg, Guilford, CT (US); Neil Beeharry, Guilford, CT (US); Paul Beckett, Yorktown Heights, NY (US); Sean Landrette, Meriden, CT (US); Chris Conrad, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 121 days.

(21) Appl. No.: 15/545,337

(22) PCT Filed: Jan. 21, 2016

(86) PCT No.: PCT/US2016/014254
§ 371 (c)(1),
(2) Date: Jul. 21, 2017

(87) PCT Pub. No.: WO2016/118709
PCT Pub. Date: Jul. 28, 2016

(65) Prior Publication Data
US 2018/0028540 A1     Feb. 1, 2018

Related U.S. Application Data

(60) Provisional application No. 62/107,263, filed on Jan. 23, 2015.

(51) Int. Cl.
| | | |
|---|---|---|
| *A61K 31/5377* | (2006.01) | |
| *A61K 31/00* | (2006.01) | |
| *A61K 38/21* | (2006.01) | |
| *A61K 45/06* | (2006.01) | |
| *A61K 31/713* | (2006.01) | |
| *A61K 39/395* | (2006.01) | |
| *C07K 16/10* | (2006.01) | |
| *C12N 15/113* | (2010.01) | |

(52) U.S. Cl.
CPC .......... *A61K 31/5377* (2013.01); *A61K 31/00* (2013.01); *A61K 31/713* (2013.01); *A61K 38/21* (2013.01); *A61K 39/39575* (2013.01); *A61K 45/06* (2013.01); *C07K 16/10* (2013.01); *C12N 15/1131* (2013.01); *C07K 2317/76* (2013.01); *C12N 2310/14* (2013.01)

(58) Field of Classification Search
None
See application file for complete search history.

(56) References Cited

U.S. PATENT DOCUMENTS

| | | |
|---|---|---|
| 7,863,270 B2 | 1/2011 | Demko et al. |
| 7,923,557 B2 | 4/2011 | Zhang et al. |
| 2007/0087008 A1 | 4/2007 | Hodge et al. |
| 2014/0294851 A1* | 10/2014 | Nguyen ............. A61K 45/06 424/141.1 |

FOREIGN PATENT DOCUMENTS

| | | | |
|---|---|---|---|
| WO | WO-2004/017950 A2 | 3/2004 | |
| WO | WO-2004/017950 A3 | 3/2004 | |
| WO | WO-2005/092924 A2 | 10/2005 | |
| WO | WO-2005/092924 A3 | 10/2005 | |
| WO | WO-2005/092924 A8 | 10/2005 | |
| WO | WO-2006/128129 A2 | 11/2006 | |
| WO | WO-2006/128129 A3 | 11/2006 | |
| WO | WO 2012/103081 * | 8/2012 | ............. A61K 39/12 |
| WO | WO-2012/103081 A1 | 8/2012 | |
| WO | WO-2015/112888 A1 | 7/2015 | |
| WO | WO-2015/187827 A1 | 12/2015 | |

OTHER PUBLICATIONS

Qiu et al. "Monoclonal Antibodies Combined with Adenovirus-Vectored Interferon Significantly Extend the Treatment Window in Ebola Virus-Infected Guinea Pigs", J. Virol. 2013; 87(13): 7754-7757.*
Mateo et al. "Knockdown of Ebola Virus VP24 Impairs Viral Nucleocapsid Assembly and Prevents Virus Replication", J. Inf. Dis. 2011; 204: S892-S896.*
Krausz et al. "A Phase IIa, Randomized, Double-Blind, Placebo-Controlled Trial of Apilimod Mesylate, an Interleukin-12/Interleukin-23 Inhibitor, in Patients With Rheumatoid Arthritis" Arthritis and Rheumatism, 2012; 64(6): 1750-1755.*
Cai, X. et al. (Jul. 25, 2013). "PIKfyve, a class III PI kinase, is the target of the small molecular IL-12/IL-23 inhibitor apilimod and a player in Toll-like receptor signaling," *Chem Biol* 20(7):912-921.
Cai, X. et al. (Apr. 1, 2014, e-published Mar. 5, 2014). "PIKfyve, a class III lipid kinase, is required for TLR-induced type I IFN production via modulation of ATF3," *J Immunol* 192(7):3383-3389.
Carette, J.E. et al. (Aug. 24, 2011). "Ebola virus entry requires the cholesterol transporter Niemann-Pick C1," *Nature* 477(7364):340-343.
Cuesta-Geijo, M.A. et al. (2012, e-published Nov. 1, 2012). "Endosomal maturation, Rab7 GTPase and phosphoinositides in African swine fever virus entry," *PLoS One* 7(11):e48853.

(Continued)

*Primary Examiner* — Stacy B Chen
(74) *Attorney, Agent, or Firm* — Muriel Liberto, Esq.; Mintz Levin Cohn Ferris Glovsky and Popeo, P.C.

(57) ABSTRACT

The present invention relates to compositions containing a PIKfyve inhibitor, preferably apilimod, APY0201 or YM-201636, most preferably apilimod, for use in treating or preventing viral infections, preferably Ebola or Marburg virus infections. It also relates to a pharmaceutical pack or kit comprising apilimod and at least one additional anti-viral agent.

16 Claims, 4 Drawing Sheets

(56) References Cited

OTHER PUBLICATIONS

Fernandes. F. et al. (Apr. 2011, e-published Feb. 1, 2011). "Phosphoinositides direct equine infectious anemia virus gag trafficking and release," *Traffic* 12(4):438-451.

Goeijenbier, M. et al. (Nov. 2014). "Ebola virus disease: a review on epidemiology, symptoms, treatment and pathogenesis," *Neth J Med* 72(9):442-448.

Hayakawa, N. et al. (Jun. 1, 2014, e-published Apr. 13, 2014). "Structure-activity relationship study, target identification, and pharmacological characterization of a small molecular IL-12/23 inhibitor, APY0201," *Bioorg Med Chem* 22(11):3021-3029.

Ikonomov, O.C. et al. (May 8, 2009, e-published Mar. 14, 2009). "YM201636, an inhibitor of retroviral budding and PIKfyve-catalyzed PtdIns(3,5)P2 synthesis, halts glucose entry by insulin in adipocytes," *Biochem Biophys Res Commun* 382(3):566-570.

Jefferies, H.B. et al. (Feb. 2008, e-published Jan. 11, 2008). "A selective PIKfyve inhibitor blocks PtdIns(3,5)P(2) production and disrupts endomembrane transport and retroviral budding," *EMBO Rep* 9(2):164-170.

Murray, J.L. et al. (Sep. 2005). "Rab9 GTPase is required for replication of human immunodeficiency virus type 1, filoviruses, and measles virus," *J Virol* 79(18)11742-11751.

International Search Report dated Mar. 14, 2016, for PCT Application No. PCT/US2016/014254, filed Jan. 21, 2016, 7 pages.

Written Opinion dated Mar. 14, 2016, for PCT Application No. PCT/US2016/014254, filed Jan. 21, 2016, 10 pages.

* cited by examiner

ANTI-VIRAL COMPOSITIONS CONTAINING PIKFYVE INHIBITORS AND USE THEREOF

RELATED APPLICATIONS

This application is a national stage entry, filed under 35 U.S.C. § 371, of International Application No. PCT/US2016/014254, filed on Jan. 21, 2016, which claims priority to U.S. Patent Application Ser. No. 62/107,263, filed on Jan. 23, 2015, the contents of which are hereby fully incorporated by reference.

FIELD OF THE INVENTION

The present invention relates to anti-viral compositions and methods of using same.

BACKGROUND OF THE INVENTION

Many viruses enter the cell via endocytosis and utilize the cell's the endosomal network as a means to infiltrate the cell and replicate. For example, viral entry into cells may be mediated by a viral glycoprotein (GP), which attaches viral particles to the cell surface, delivers them to endosomes, and catalyzes fusion between viral and endosomal membranes. For example, Rab9 GTPase was shown to be required for replication of HIV-1, filoviruses (such as Ebola and Marburg), and measles virus. Murray et al. 2005 *J. Virology* 79:11742-11751. Silencing Rab9 expression dramatically inhibited HIV replication, as did silencing the host genes encoding TIP47, p40, and PIKfyve, which also facilitate late-endosome-to-trans-Golgi vesicular transport. Reducing Rab9 expression also inhibited the replication of the enveloped Ebola and Marburg filoviruses and that of measles virus, but not the non-enveloped reovirus. US 20070087008 (Hodge et al.) describes RAB9A, RAB11A, and modulators of those proteins as potentially useful for decreasing viral replication, especially HIV replication.

Additional studies indicate that the endo/lysosomal cholestrol transporter Niemann-Pick C1 (NPC1) acts as a post-endocytic intracellular receptor that is necessary for Ebola and Marburg virus penetration. Carette et al., 2011 *Nature* 477:340. Niemann-Pick C1 (NPC1) and the homotypic fusion and vacuole protein sorting (HOPS) complex were identified in a genome-wide haploid genetic screen as host factors for filovirus entry. The NPC1 locus was the single strongest hit, with 39 independent insertions. The HOPS complex was the next strongest hit. Additional genes whose products are involved in the biogenesis of endosomes (PIKfyve) and lysosomes (BLOC1S1, BLOC1S2), and in the targeting of luminal cargo to the endocytic pathway (GNPTAB) were also identified, but only NPC1 was validated in functional assays. For example, NPC1 function was required for infection by Ebola and Marburg viruses in human fibroblasts, NPC1 deficiency conferred resistance to viral infection in HAP1 and CHO cells, and NPC1 null mice were resistant to infection and pathogenesis of Ebola and Marburg viruses. WO 2012/103081 (Chandran et al.) describes methods for treating filovirus infection using an agent that inhibits, inter alia, NPC1 and the HOPS.

In yeast, fusion of the phagosome membrane to the lysosome membrane requires the HOPs complex and phosphatidylinositol 3,5-bisphosphate $(PI(3,5)P_2)$. Synthesis of $PI(3,5)P_2$ is mediated by phosphatidylinositol-3-phosphate 5-kinase (PIKfyve). Phosphoinositides such as $PI(3,5)P_2$ are important lipid regulators of membrane trafficking and cellular signaling. Using the inhibitor YM201636, Jefferies et al. showed that inhibiting PIKfyve and blocking cellular production of $PI(3,5)P_2$ disrupts endomembrane transport and retroviral budding. Jefferies et al. *EMBO rep.* 2008 9:164-170.

Ebola is a filamentous, lipid enveloped, negative stranded RNA virus of the family Filoviridae. There are five known strains of Ebola, four of which infect humans. The 5 strains are Bundibugyo, Sudan, Tai Forest, Zaire, or Reston; Reston is not known to infect humans. Zaire or Ebola virus is responsible for the majority of outbreaks (Burd, 2015). Initially Ebola targets macrophages and dendritic cells (Missai and Sullivan 2014); however, it is subsequently able to penetrate all cell types excluding lymphocytes by binding to the plasma membrane surface proteins. Viral entry is mediated by glycoprotein (GP), which attaches viral particles to the cell surface, delivers viral particles to the endosomes; and catalyzes fusion between the viral particles and the endosomal membranes (Gray, 2014, Cook and Lee, 2013, Ansari, 2014, Carette, et al. 2012).

EVD is global public health emergency and the World Health Organization has declared the recent epidemic to be a Public Health Emergency of International Concern. The NIH classifies EVD as a Category A pathogen which indicates that it poses the highest risk to public safety and national security (Stahelin, 2014). The recent West African outbreak was first reported in March 2014 (McCoy, et al. 2014, Meyers et al. 20152015, Gatherer, 2014, Ansari, 2014) with infection rates increasing by 13% in a 6 month period. The recent epidemic is concentrated in areas of West Africa in countries such as Guinea, Liberia, Nigeria, Senegal, and Sierra Leone. The current outbreak has killed over 3,800 people (documented cases) making it the most lethal outbreak of Ebola to date. In the recent outbreak, mortality rates are approximately 50% to 70%; while mortality rates in the 20 recognized outbreaks of Ebola range from 25 to 90% (Meyers et al. 2015). Clinical manifestations, duration of illness, case fatality rates and the degree of transmission rates in this outbreak are similar to previous outbreaks. Due to global travel and the international aid workers who have been on the ground in West Africa, infected people have traveled outside of West Africa. Countries such as the United Kingdom, Canada, Spain and the United States have allowed infected patients to re-enter and receive treatment. On Sep. 30, 2014, the CDC confirmed the first case of travel associated EVD in the US. Subsequently, two health care workers who were exposed to EVD through this initial patient, tested positive for EVD; these two cases were the first non-travel related cases of EVD in the United States.

EVD is initially transmitted to man through contact with an infected animal. The virus is spread in humans from direct contact with broken skin or mucous membranes with blood and body fluids including urine, saliva, feces, vomit, breast milk and semen; needles and syringes that are contaminated with the virus; or infected animals. EVD is not spread through the air, water or food nor is it believed to be transmitted through mosquitoes or other insect vectors. Symptoms of EVD may appear 2 to 21 days after exposure with an average of 10 days. During the latent period of the disease the patient may not show symptoms and is considered noncontagious.

Initial clinical signs of Ebola consist of: Fever (>38.6° C. or 101.5° F.), severe headache, muscle pain, weakness, diarrhea, vomiting, abdominal pain, and unexplained hemorrhage.

Over the clinical course of Ebola, patients can develop fulminant septic shock and coagulopathy which can subsequently lead to death. EVD is often masked upon clinical presentation because the early signs and symptoms of EVD are similar to other common viral infections; therefore, patient histories are critical to understanding the potential risk of EVD. Several diagnostic tests are available for Ebola; including RT-PCR and ELISA tests (Burd, 2015; Bishop 2014); however, none of these tests are available in a non-hospital setting; therefore, making confirmation of the diagnosis difficult in the field. EVD care is generally limited to supportive care including administration of IV fluids, maintenance of oxygen status and blood pressure and treatment other underlying conditions or organ dysfunction or failure. Recovery from EVD is dependent on the supportive care and immune response of the patient.

Currently, there are no approved therapies for EVD. Two experimental treatments for Ebola are available on an emergency use basis in the US. They are ZMAPP (MAPP Pharmaceuticals) which is a biologic composed of three humanized monoclonal antibodies and TKM-Ebola, (Tekmira) a siRNA which interferes with the viral proteins L, VP24, and VP35 (Bishop 2014).). The efficacy of both of these experimental agents has yet to be established in controlled clinical trials. Current supplies of ZMAPP are exhausted and the drug product requires frozen shipment while TKM-Ebola is on partial clinical hold due to safety issues; therefore, there exists an urgent medical need for the development of new safe and effective treatments.

The present invention addresses the need for antiviral compositions and methods for the treatment of subjects infected with viruses and the prophylaxis of subjects who are at risk for viral infection, and particularly for human subjects infected with or at risk of infection with Ebola virus.

SUMMARY OF THE INVENTION

The present invention provides compositions and methods related to the use of PIKfyve inhibitors for the treatment and/or prophylaxis of viral infections in a subject, preferably a human subject, in need of such treatment or prevention. In one aspect, the present invention is based upon the premise that inhibitors of the cellular PIP complex protein, PIKfyve, represent promising candidate anti-virals for the treatment of infections by Ebola and Marburg filoviruses. This is based upon the unexpected finding that it is possible to attain relatively high and sustained plasma concentrations of a PIKfyve inhibitor, apilimod, in mammals, concentrations that greatly exceed the amount of apilimod needed to inhibit PIKfyve and disrupt intracellular trafficking, which is crucial for successful infection by viruses such as Marburg and Ebola. Moreover, the present disclosure demonstrates that apilimod blood plasma levels as high as XX for [time] were achievable and without observable adverse effects in mice.

In one embodiment, the invention provides a method for treating or preventing a viral infection in a subject in need thereof, the method comprising administering to the subject a composition comprising a therapeutically effective amount of at least one PIKfyve inhibitor. In one embodiment, the at least one PIKfyve inhibitor is selected from the group consisting of apilimod, APY0201, and YM-201636. In one embodiment, the at least one PIKfyve inhibitor is apilimod. In one embodiment, the at least one PIKfyve inhibitor comprises one or more apilimod compositions selected from apilimod free base or pharmaceutically acceptable salts, solvates, clathrates, hydrates, polymorphs, prodrugs, analogs or derivatives thereof. In one embodiment, the PIKfyve inhibitor comprises one or more of an apilimod composition, an active metabolite of apilimod, and combinations thereof.

In one embodiment, the apilimod composition comprises apilimod free base or apilimod dimesylate.

In one embodiment of the methods described herein, the apilimod composition is combined with at least one additional active agent in a single dosage form.

In one embodiment, the viral infection is caused by an Ebola virus or a Marburg virus. In one embodiment, the virus is an Ebola virus. In one embodiment, the Ebola virus belongs to a strain selected from the group consisting of the Bundibugyo, Sudan, Tai Forest, and Zaire strains. In one embodiment, the Ebola virus is a Zaire ebola virus.

In one embodiment, the apilimod is administered orally, for example in the form of a tablet or capsule. In one embodiment, the apilimod is administered injection or by addition to sterile infusion fluids for intravenous infusion and is in the form of a suitable sterile aqueous solution or dispersion.

In one embodiment, the therapeutically effective amount of apilimod in humans is from about 70 to 1000 mg/day, from about 70 to 500 mg/day, from about 70 to 250 mg/day, from about 70 to 200 mg/day, from about 70 to 150 mg/day, of from about 70 to 100 mg/day.

The present invention also provides methods of treating or preventing a viral infection, or ameliorating one or more symptoms or complications of a viral infection, by administering to a subject, preferably a human subject, a composition comprising an effective amount of at least on PIKfyve inhibitor and further comprising administering to the subject at least one additional anti-viral agent, either in the same composition as the at least one PIKfyve inhibitor, or in a different composition, for example in a therapeutic regiment as part of a combination therapy for treatment of the viral infection. In one embodiment, the at least one additional anti-viral agent comprises an antibody or a combination of antibodies, preferably human or humanized antibodies, but chimeric (e.g., mouse-human chimeras) antibodies are also acceptable. In one embodiment, the at least one additional anti-viral agent comprises a small interfering RNA (siRNA) or a combination of siRNA molecules. In one embodiment, the siRNA or combination of siRNA molecules targets one or more Ebola virus proteins. In one embodiment, the one or more Ebola virus proteins is selected from the group consisting of the Zaire Ebola L polymerase, Zaire Ebola membrane-associated protein (VP24), and Zaire Ebola polymerase complex protein (VP35). In one embodiment, the siRNA or combination of siRNA molecules targets all three of these proteins.

In the methods described here, the at least one PIKfyve inhibitor can be administered by any suitable route and either in the same dosage form or in a different dosage form from the optional additional anti-viral agent or other optional therapeutic agent as described infra. In one embodiment, administration is via an oral, intravenous, or subcutaneous route. In one embodiment, the administration of the at least one PIKfyve inhibitor is once daily, twice daily, or continuous for a period of time, for example one or several days or one or several weeks. Continuous administration may be performed, for example, by using slow release dosage form that is e.g., implanted in the subject, or via continuous infusion, for example using a pump device, which also may be implanted.

In one embodiment, the at least one PIKfyve inhibitor is an apilimod composition and the apilimod composition is administered in an amount of 70 to 1000 mg/day. In one embodiment, administration is effective to achieve a plasma concentration of the PIKfyve inhibitor in the subject in the range of from 50 to 1000 nM.

In accordance with the methods described herein, the effective amount of the PIKfyve inhibitor administered is, for example, an amount effective to prevent or ameliorate a cytokine storm in the subject, inhibit or reduce the rate of viral replication in the subject, and/or stabilize or reduce the viral load of the subject.

The invention also provides a pharmaceutical pack or kit comprising, in separate containers or in a single container, a unit dose of an apilimod composition and a unit dose of at least one additional anti-viral agent. In one embodiment, the pharmaceutical pack or kit comprises at least one PIKfyve inhibitor that is an apilimod composition selected from apilimod free base, apilimod dimesylate, or a racemically pure enantiomer of an active metabolite of apilimod, and combinations thereof.

BRIEF DESCRIPTION OF THE DRAWINGS

FIG. 1: Apilimod binds with high affinity to PIKfyve (Kd=75 pM).

FIG. 2: Apilimod induces vacuolization of a representative cancer cell line. Left: Untreated cell. Right: Live cells treated with 500 nM apilimod 24 h.

FIG. 3: Mean Plasma Apilimod (API) or Plasma Total Apilimod Effect Concentration (TEAC) in ng/mL versus Time. Apilimod free base was administered in two 105 mg doses, 10 hours apart.

FIG. 4: In vitro activity of apilimod dimesylate against Ebola virus.

DETAILED DESCRIPTION OF THE INVENTION

The present invention provides compositions and methods related to the use of PIKfyve inhibitors for treating or preventing a viral infection in a subject, preferably a human subject, in need of such treatment or prevention.

In one embodiment, the invention provides methods for the treatment of viral infections in a subject iby administering to the subject a therapeutically effective amount of at least one PIKfyve inhibitor. In one embodiment, the invention provides pharmaceutical compositions comprising a therapeutically effective amount of at least one PIKfyve inhibitor. In one embodiment, the at least one PIKFyve inhibitor is selected from the group consisting of apilimod, APY0201, and YM201636, or a pharmaceutically acceptable salt, solvate, clathrate, hydrate, polymorph, metabolite, prodrug, analog or derivative thereof.

In one embodiment, the viral infection is caused by a virus selected from the group consisting of measles, Ebola (EboV), Marburg (MarV), borna disease, and human immunodeficiency virus (HIV), severe acute respiratory system virus (SARS), and middle east respiratory syndrome virus (MERS). In one embodiment, the viral infection is caused by EboV or MarV.

In one embodiment, the at least one PIKfyve inhibitor is apilimod. Apilimod is a selective inhibitor of PIKfyve (Cai et al. 2013 *Chem. & Biol.* 20:912-921). Based upon its ability to inhibit IL-12/23 production, apilimod has been suggested as useful for treating inflammatory and autoimmune diseases such as rheumatoid arthritis, sepsis, Crohn's disease, multiple sclerosis, psoriasis, or insulin dependent diabetes mellitus, and in cancers where these cytokines were believed to play a pro-proliferative role.

As used herein, the term "an apilimod composition" may refer to a composition comprising apilimod itself (free base), or may encompass pharmaceutically acceptable salts, solvates, clathrates, hydrates, polymorphs, prodrugs, analogs or derivatives of apilimod, as described below. The structure of apilimod is shown in Formula I:

(I)

The chemical name of apilimod is 2-[2-Pyridin-2-yl)-ethoxy]-4-N'-(3-methyl-benzilidene)-hydrazino]-6-(morpholin-4-yl)-pyrimidine (IUPAC name: (E)-4-(6-(2-(3-methylbenzylidene)hydrazinyl)-2-(2-(pyridin-2-yl)ethoxy) pyrimidin-4-yl)morpholine), and the CAS number is 541550-19-0.

Apilimod can be prepared, for example, according to the methods described in U.S. Pat. Nos. 7,923,557, and 7,863, 270, and WO 2006/128129.

In one embodiment, the apilimod composition for use in the compositions and methods of the invention is the free base or dimesylate salt form, MW 610.7 (dimesylate salt); tPSA 83.1; pKa 5.39 (±0.03), 4.54 (±0.27); HBD 1. The apilimod dimesylate salt is highly water soluble (>25 mg/mL) and shows moderate permeability (>70% in rats). In one embodiment, the apilimod composition for use in the compositions and methods of the invention is an active metabolite of apilimod. Six primary metabolites were identified in rat and human microsomal and hepatocyte stability studies. Human, rat, rabbit and dog studies showed a qualitatively similar metabolic profile. $T_{max}$ generally occurred within 1 or 2 hours after the oral dose, consistent with the rapid elimination of this compound from the circulation. Reaction phenotyping studies indicated that CYP3A4 and to a lesser extent CYP1A2 and/or CYP2D6, contribute to metabolism. The primary metabolites are short-lived in circulation. Both apilimod free base and the dimesylate salt are highly bound (>99%) to rat, dog and human plasma proteins.

In one embodiment, the at least one PIKfyve inhibitor is selected from APY0201, and YM-201636. The structures of APY0201 and YM-201636 are shown in Formula II and Formula III respectively.

(II)

APY0201

YM-201636

The chemical name of APY0201 is (E)-4-(5-(2-(3-methylbenzylidine)hydrazinlyl)-2-(pyridine-4-yl)pyrazolol[1,5-a]pyrimidin-7-yl)morpholine. APY0201 is a selective PIKfyve inhibitor (Hayakawa et al. 2014 *Bioorg. Med. Chem.* 22:3021-29). APY0201 directly interacts with the ATP-binding site of PIKfyve kinase, which leads to suppression of PI(3,5)P$_2$ synthesis, which in turn suppresses the production of IL-12/23.

The chemical name for YM201636 is 6-amino-N-(3-(4-morpholinopyrido[3',2':4,5]furo[3,2-d]pyrimidin-2-yl)phenyl)nicotinamide (CAS number is 371942-69-7). YM201636 is a selective inhibitor of PIKfyve (Jefferies et al. *EMBO rep.* 2008 9:164-170). It reversibly impairs endosomal trafficking in NIH3T3 cells, mimicking the effect produced by depleting PIKfyve with siRNA. YM201636 also blocks retroviral exit by budding from cells, apparently by interfering with the endosomal sorting complex required for transport (ESCRT) machinery. In adipocytes, YM-201636 also inhibits basal and insulin-activated 2-deoxyglucose uptake (IC$_{50}$=54 nM).

As used herein, the term "pharmaceutically acceptable salt," is a salt formed from, for example, an acid and a basic group of an apilimod composition. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In a preferred embodiment, the salt of apilimod comprises methanesulfonate.

The term "pharmaceutically acceptable salt" also refers to a salt prepared from an apilimod composition having an acidic functional group, such as a carboxylic acid functional group, and a pharmaceutically acceptable inorganic or organic base.

The term "pharmaceutically acceptable salt" also refers to a salt prepared from an apilimod composition having a basic functional group, such as an amino functional group, and a pharmaceutically acceptable inorganic or organic acid.

The salts of the compounds described herein can be synthesized from the parent compound by conventional chemical methods such as methods described in Pharmaceutical Salts: Properties, Selection, and Use, P. Hemrich Stalil (Editor), Camille G. Wermuth (Editor), ISBN: 3-90639-026-8, August 2002. Generally, such salts can be prepared by reacting the parent compound with the appropriate acid in water or in an organic solvent, or in a mixture of the two.

One salt form of a compound described herein can be converted to the free base and optionally to another salt form by methods well known to the skilled person. For example, the free base can be formed by passing the salt solution through a column containing an amine stationary phase (e.g. a Strata-NH2 column). Alternatively, a solution of the salt in water can be treated with sodium bicarbonate to decompose the salt and precipitate out the free base. The free base may then be combined with another acid using routine methods.

As used herein, the term "polymorph" means a solid crystalline form of a compound of the present invention. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein, the term "prodrug" means a derivative of a compound described herein that can hydrolyze, oxidize, or otherwise react under biological conditions (in vitro or in vivo) to provide a compound of the invention. Prodrugs may only become active upon such reaction under biological conditions, or they may have activity in their unreacted forms. Examples of prodrugs contemplated in this invention include, but are not limited to, analogs or derivatives of a compound described herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

In addition, some of the compounds suitable for use in the methods of in this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention can also be represented in multiple tautomeric forms, in such instances, the invention expressly includes all tautomeric forms of the compounds described herein (e.g., there may be a rapid equilibrium of multiple structural forms of a compound), the invention expressly includes all such reaction products). All such isomeric forms of such compounds are expressly included in the present invention. All crystal forms of the compounds described herein are expressly included in the present invention.

As used herein, the term "solvate" or "pharmaceutically acceptable solvate," is a solvate formed from the association of one or more solvent molecules to one of the compounds disclosed herein. The term solvate includes hydrates (e.g., hemi-hydrate, mono-hydrate, dihydrate, trihydrate, tetrahydrate, and the like).

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Methods of Treatment

The present invention provides methods for the treatment of viral infections in a subject in need thereof by administering to the subject a therapeutically effective amount of at least one PIKfyve inhibitor. In one embodiment, the at least one PIKfyve inhibitor is selected from an apilimod composition, APY0201, YM-201636 or a pharmaceutically acceptable salt, solvate, clathrate, hydrate, polymorph, metabolite, prodrug, analog or derivative thereof. The present invention further provides the use of at least one PIKfyve inhibitor for the preparation of a medicament useful for the treatment of viral infections.

The term "therapeutically effective amount" refers to an amount of a PIKfyve inhibitor sufficient to treat, ameliorate a symptom of, reduce the severity of, or reduce the duration of a viral infection, or enhance or improve the therapeutic effect of another therapy, e.g., another antiviral therapy, when administered in combination with the PIKfyve inhibitor or as part of a therapeutic regimen that includes administering a PIKfyve inhibitor.

In one embodiment, the therapeutically effective amount is an amount effective to achieve one or more of the following: inhibit cellular PIKfyve activity, substantially prevent viral entry into a subject's cells, reduce the amount of viral particles which gain entry to a subject's cells, reduce viral replication within the subject's cells, ameliorate one or more symptoms associated with viral infection of the subject, and reduce the severity of one or more symptoms associated with viral infection of the subject.

In one embodiment, the therapeutically effective amount is an amount sufficient to reduce the magnitude of, or prevent the onset, of a cytokine storm in the subject.

In one embodiment, the therapeutically effective amount is an amount sufficient to reduce viral load. In one embodiment, the viral load is reduced by 5% or greater, 10% or greater, 20% or greater, 30% or greater, 40% or greater, 50% or greater, or 75% or greater. In one embodiment, the viral load is reduced by at least 0.5 log units, at least 1 log unit, at least 2 log units, at least 3 log units, at least 4 log units, at least 10 log units, at least 15 log units, or by at least 20 log units.

An effective amount can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In one embodiment, the therapeutically effective amount of apilimod in humans is from about 70 to 1000 mg/day, from about 70 to 500 mg/day, from about 70 to 250 mg/day, from about 70 to 200 mg/day, from about 70 to 150 mg/day, of from about 70 to 100 mg/day.

In one embodiment, the method comprises administering to a subject a therapeutically effective amount of a PIKfyve inhibitor as monotherapy for the treatment of a viral infection. In another embodiment, described more fully below, the PIKfyve inhibitor, or more than one PIKfyve inhibitor, is administered as part of a combination therapy or therapeutic regimen, for example with one or more anti-viral agents or an anti-viral regimen.

The methods may comprise administering the PIKfyve inhibitor according to a specified dosing schedule or therapeutic regimen. For example, the PIKfyve inhibitor can be administered once daily or from two to five times daily. In one embodiment, apilimod, APY0201, or YM-201636 is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In the context of the methods described herein, the amount of a PIKfyve inhibitor, preferably an apilimod composition, administered to the subject is a therapeutically effective amount. The term "therapeutically effective amount" refers to an amount sufficient to treat, ameliorate a symptom of, reduce the severity of, or reduce the duration of the disease or disorder being treated, or enhance or improve the therapeutic effect of another therapy, or sufficient to exhibit a detectable therapeutic effect in the subject. In one embodiment, the therapeutically effective amount of a PIKfyve inhibitor, preferably an apilimod composition, is the amount effective to inhibit PIKfyve kinase activity.

An effective amount of a PIKfyve inhibitor, preferably an apilimod composition, can range from about 0.001 mg/kg to about 1000 mg/kg, about 0.01 mg/kg to about 100 mg/kg, about 10 mg/kg to about 250 mg/kg, about 0.1 mg/kg to about 15 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See e.g., U.S. Pat. No. 7,863,270, incorporated herein by reference.

In more specific aspects, a PIKfyve inhibitor, preferably an apilimod composition, is administered at a dosage regimen of 70-1000 mg/day (e.g., 70, 75, 80, 85, 90, 95, 100, 125, 125, 150, 175, 200, 225, 250, 275, 300, 350, 400, 450, 500, 550, 600, 650, 700, 750, 800, 850, 900, 950, or 1000 mg/day) for at least 1 week, in some embodiments for 1 to 4 weeks, from 2 to 6 weeks, from 2 to 8 weeks, from 2 to 10 weeks, or from 2 to 12 weeks, 2 to 16 weeks, or longer (e.g., 1, 2, 3, 4, 5, 6, 7, 8, 9, 10, 11, 12, 36, 48, or more weeks). In one embodiment, a PIKfyve inhibitor, preferably an apilimod composition, is administered at a dosage regimen of 70-1000 mg/day for 2, 4, 12, or 16 weeks. Alternatively or subsequently, a PIKfyve inhibitor, preferably an apilimod composition, is administered at a dosage regimen of 35 mg-500 mg twice a day for 4 weeks, 8 weeks, 12 weeks, 16 weeks, or longer.

An effective amount of the PIKfyve inhibitor can be administered once daily, twice daily, from two to five times daily, up to two times or up to three times daily, or up to eight times daily. In one embodiment, the inhibitor is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In accordance with the methods described herein, a "subject in need of" is a subject having a viral disease, or a subject having an increased risk of developing a viral disease, relative to the population at large. The subject in need thereof can be one that is "non-responsive" or "refractory" to a currently available therapy for the viral disease. In this context, the terms "non-responsive" and "refractory" refer to the subject's response to therapy as not clinically adequate to relieve one or more symptoms associated with the viral infection. In one aspect of the methods described here, the subject in need thereof is a subject having a viral disease caused by an Ebola or Marburg virus who is refractory to standard therapy.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The term "patient" refers to a human subject.

The present invention also provides a monotherapy for the treatment of a viral disease, as described herein. As used herein, "monotherapy" refers to the administration of a single active or therapeutic compound to a subject in need thereof.

As used herein, "treatment", "treating" or "treat" describes the management and care of a patient for the purpose of combating a viral disease and includes the administration of a PIKfyve inhibitor, preferably an apilimod composition, to alleviate the symptoms or complications of the viral disease.

As used herein, "prevention", "preventing" or "prevent" describes reducing or eliminating the onset of the symptoms or complications of the viral disease, includes the administration of a PIKfyve inhibitor, preferably an apilimod composition, to reduce the onset, development or recurrence of symptoms of the viral disease.

Combination Therapies

The present invention also provides methods comprising combination therapy. As used herein, "combination therapy" or "co-therapy" includes the administration of a therapeutically effective amount of a PIKfyve inhibitor, preferably an apilimod composition, with at least one additional active agent, as part of a specific treatment regimen intended to provide a beneficial effect from the co-action of the active agents in the regimen. "Combination therapy" is not intended to encompass the administration of two or more therapeutic compounds as part of separate monotherapy regimens that incidentally and arbitrarily result in a beneficial effect that was not intended or predicted.

Thus, the invention provides methods of treating a subject for a viral disease or viral infection (the terms "viral disease" and "viral infection" are used interchangeably herein) using a combination therapy comprising a PIKfyve inhibitor, preferably an apilimod composition, and at least one additional active agent in an anti-viral regimen for the treatment of the viral disease.

The at least one additional active agent may be a therapeutic agent, for example an anti-viral agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to non-therapeutic agents, the beneficial effect of the combination may relate to the mitigation of a toxicity, side effect, or adverse event associated with a therapeutically active agent in the combination.

In one embodiment, the at least one additional agent is a non-therapeutic agent which mitigates one or more side effects of an apilimod composition, the one or more side effects selected from any of nausea, vomiting, headache, dizziness, lightheadedness, drowsiness and stress. In one aspect of this embodiment, the non-therapeutic agent is an antagonist of a serotonin receptor, also known as 5-hydroxytryptamine receptors or 5-HT receptors. In one aspect, the non-therapeutic agent is an antagonist of a 5-HT3 or 5-HT1a receptor. In one aspect, the non-therapeutic agent is selected from the group consisting of ondansetron, granisetron, dolasetron and palonosetron. In another aspect, the non-therapeutic agent is selected from the group consisting of pindolol and risperidone.

In one embodiment, the at least one additional agent is a therapeutic agent. In one embodiment, the therapeutic agent is selected from an anti-viral agent, an anti-viral vaccine, a nucleotide analogue, a cytokine (e.g., an interferon), and an immunoglobulin, and combinations thereof. In one embodiment, the at least one additional agent is selected from an inhibitor of one or more of NPCI, VPSII, VPSI6, VPSI8, VPS33A, VPS39, VPS41, BLOCISI, BLOCIS2, GNPT-AB, PIKFYVE, ARGHGAP23, COPI, COPII, TIP47, P40, Rab GTP-binding proteins (e.g., Rab9), clathrin, AP1, AP3, t-/v-SNARE complex, ARFs, Ras GTP-ases, and a combinations thereof. In one embodiment, the at least one additional therapeutic agent is selected from an antibody, a PIKfyve inhibitor, and an inhibitor of phosphotransferase activity.

Non-limiting examples of anti-viral agents that may be used in combination with a PIKfyve inhibitor as described herein include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

In certain embodiments the at least one PIKfyve inhibitor is provided in a single dosage form in combination with one or more additional therapeutic agents. In one embodiment, the at least one PIKfyve inhibitor is an apilimod composition and the therapeutic agent is an antiviral agent. In another embodiment, the apilimod is provided in combination with one or more additional PIKfyve inhibitors, for example APY0201 and YM201636. Where more than one therapeutic agent is present in a single dosage form, the therapeutically effective amount is based upon the total amount of therapeutic agents in the dosage form.

In one embodiment the at least one PIKfyve inhibitor is provided in a separate dosage form from the one or more additional therapeutic agents. Separate dosage forms are desirable, for example, in the context of a combination therapy in which the therapeutic regimen calls for administration of different therapeutic agents at different frequencies or under different conditions, or via different routes.

In one embodiment, administration of the at least one PIKfyve inhibitor as described herein is accomplished via an oral dosage form suitable for oral administration. In another embodiment administration is by an indwelling catheter, a pump, such as an osmotic minipump, or a sustained release composition that is, for example, implanted in the subject.

Pharmaceutical Compositions and Formulations

The present invention provides pharmaceutical compositions comprising an effective amount of at least one PIKfyve inhibitor and at least one pharmaceutically acceptable excipient or carrier, wherein the effective amount is as described above in connection with the methods of the invention.

In one embodiment, the PIKfyve inhibitor is selected from one or more of an apilimod composition as described above, APY0201, YM-201636, and pharmaceutically acceptable salts, solvates, clathrates, hydrates, polymorphs, metabolites, prodrugs, analogs and derivatives thereof. In one embodiment, the PIKfyve inhibitor is an apilimod composition.

In one embodiment, the at least one PIKfyve inhibitor is combined with at least one additional therapeutic agent in a single dosage form. In one embodiment, the at least one additional therapeutic agent is selected from an anti-viral agent (as described above), an anti-viral vaccine, a nucleotide analogue, a cytokine (e.g., an interferon), and an immunoglobulin, and combinations thereof. In one embodiment, the at least one additional therapeutic agent is selected from an inhibitor of one or more of NPCI, VPSII, VPSI6, VPSI8, VPS33A, VPS39, VPS41, BLOCISI, BLOCIS2, GNPT-AB, PIKFYVE, ARGHGAP23, COPI, COPII, TIP47, P40, Rab GTP-binding proteins (e.g., Rab9), clathrin, AP1, AP3, t-/v-SNARE complex, ARFs, Ras GTP-ases, and a combinations thereof. In one embodiment, the additional therapeutic agent is selected from an antibody, a PIKfyve inhibitor, and an inhibitor of phosphotransferase activity.

The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). Exemplary doses and dosages regimens for the compositions in methods of treating viral infections are described above.

A dose may be provided in unit dosage form. For example, the unit dosage form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention, one or more syringes, one or more applicators, or a sterile solution suitable for reconstituting a pharmaceutical composition of the present invention.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1: Apilimod is a Highly Selective Binder of PIKfyve Kinase

Figure 1:
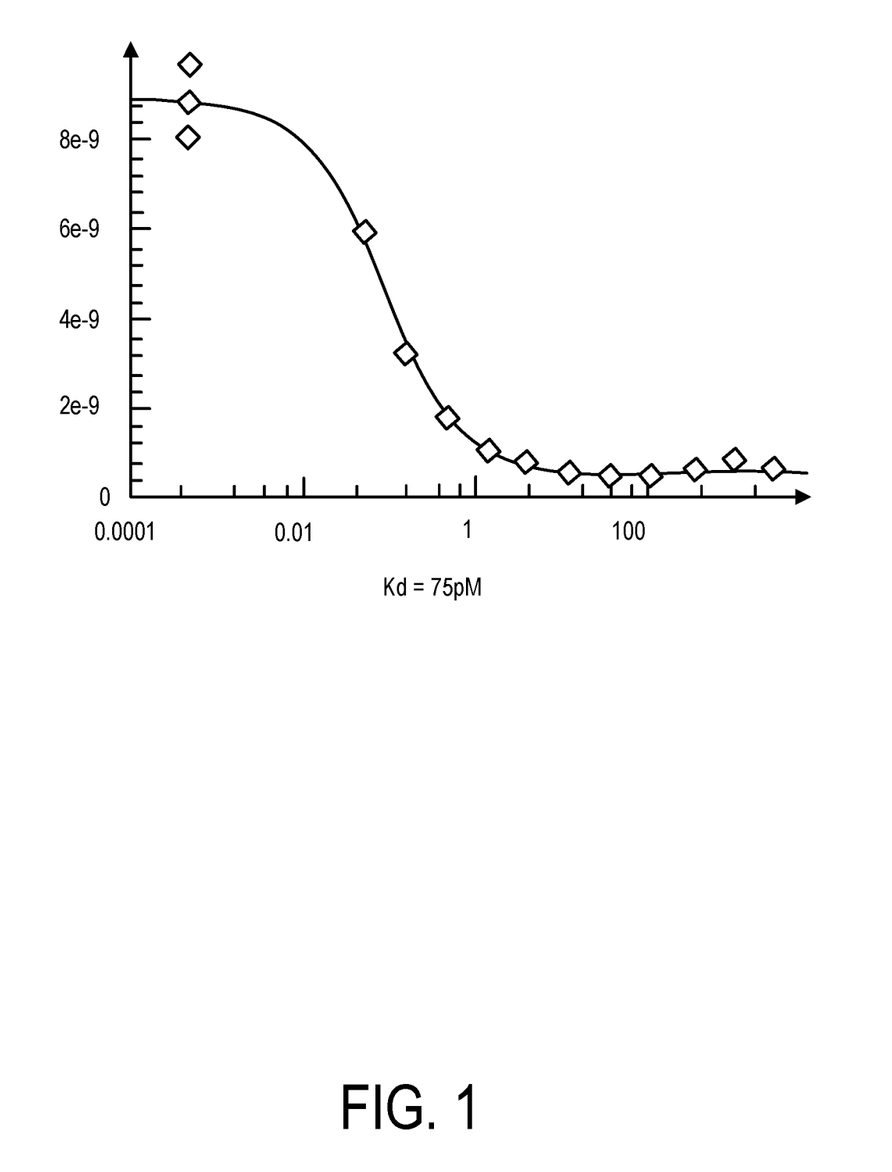

Protein kinase profiling of apilimod was conducted to identify kinase targets (DiscoveRx, Fremont, Calif.). A dissociation constant (Kd) study was performed using apilimod at increasing concentrations (0.05-3000 nM) against PIKfyve, a known target of apilimod. The experiment was performed in duplicate and the Kd was determined to be 0.075 nM (range 0.069-0.081 nM) (see FIG. 1).

Apilimod was also screened against a comprehensive panel of kinases (PIKfyve not included). In total, 456 kinases, including disease-relevant kinases, were assayed for their ability to bind with apilimod. The screening concentration of apilimod was 1 mM, a concentration that is >10,000 times greater than the Kd for apilimod against PIKfyve. The results from the screen showed that apilimod did not bind to any of the 456 kinases tested.

Together, these results demonstrate that apilimod binds with high selectivity to a single cellular kinase, PIKfyve.

Figure 2:
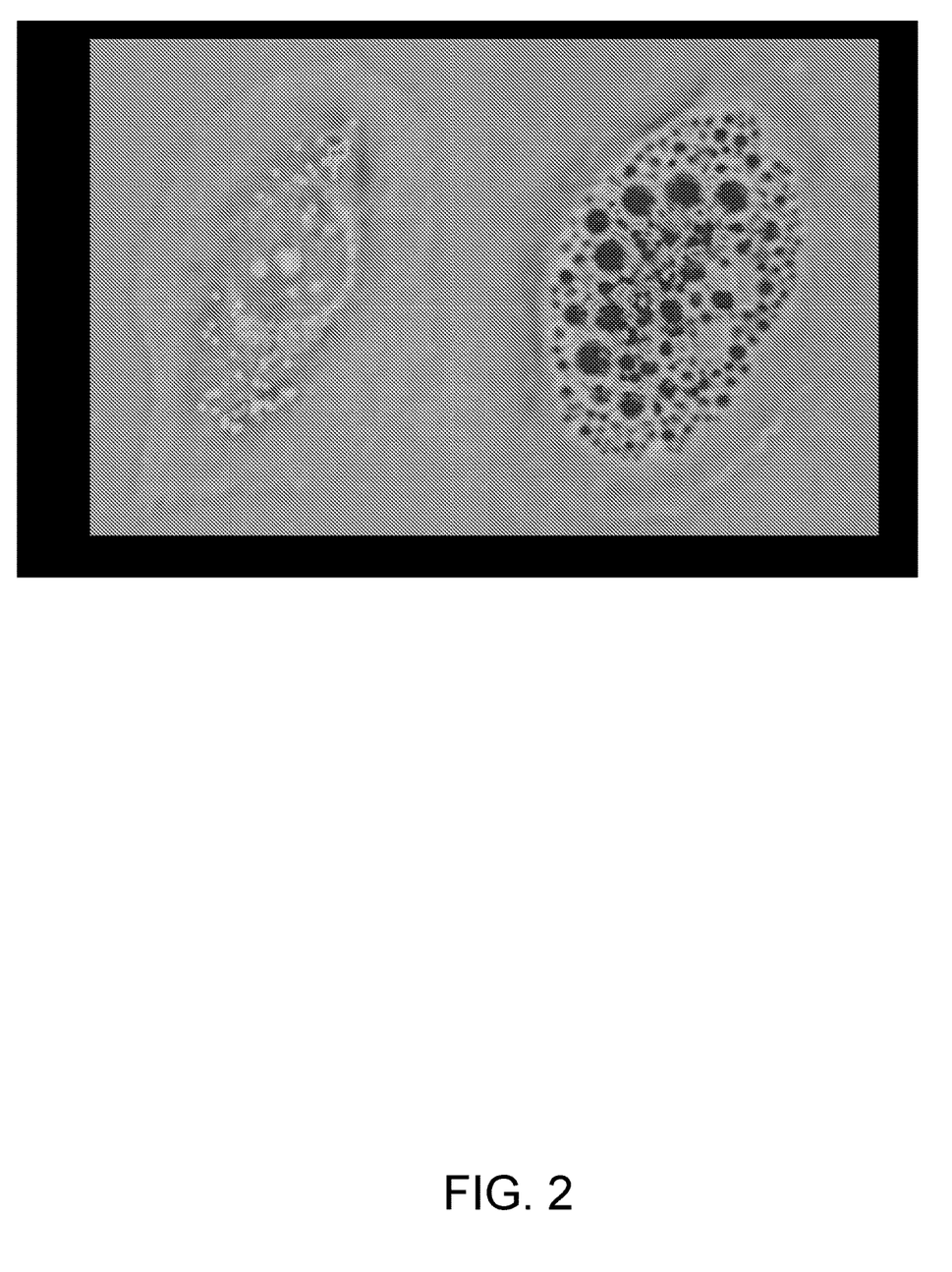
Figure 3:
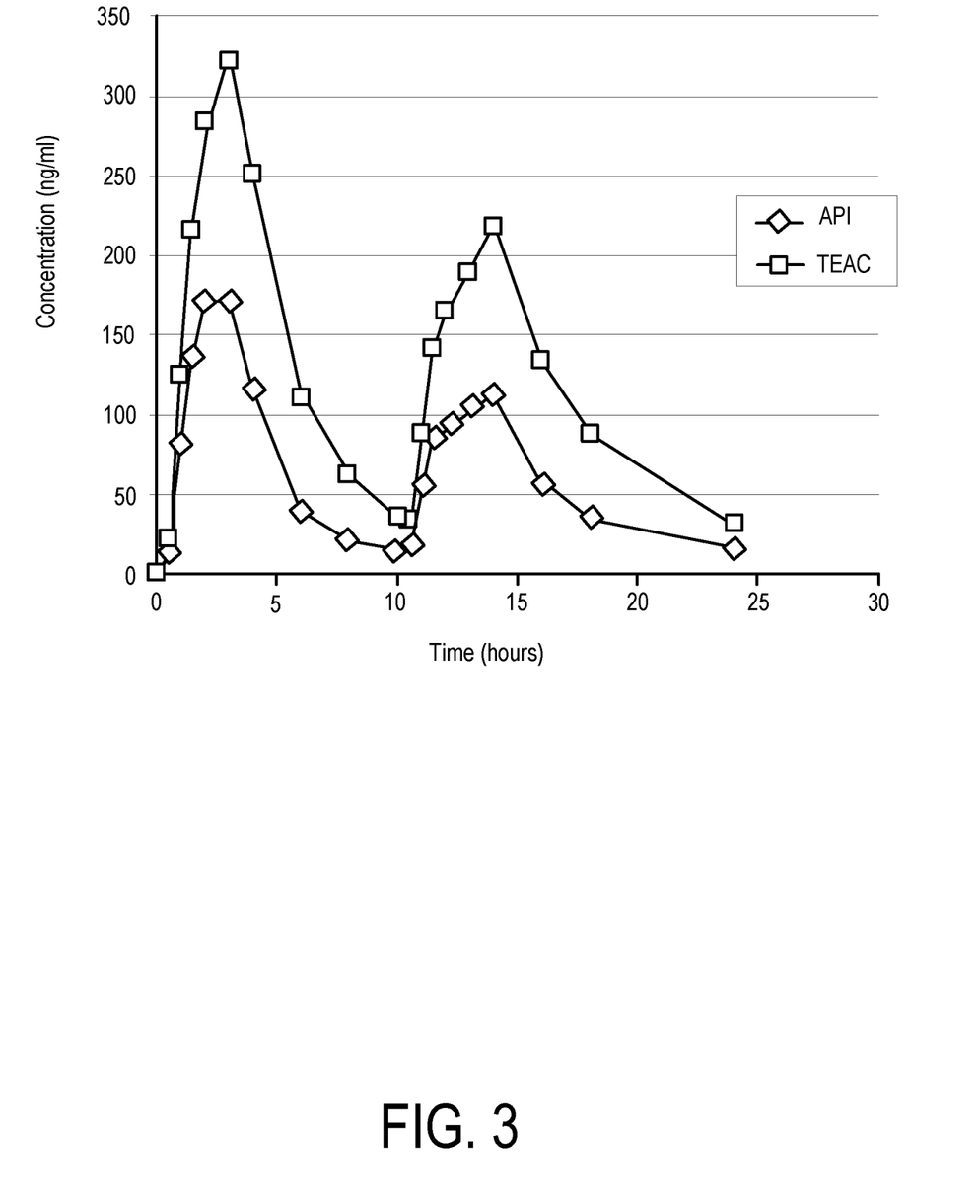

Example 2: Apilimod Induces Vacuolization and Disrupts Intracellular Traficking in Cells Apilimod has been demonstrated to be a potent and specific inhibitor of the phosphoinositide kinase PIKfyve, an enzyme that binds to PI(3)P and catalyzes the formation of the lipid second messengers PI(3,5)P2 and PI(5)P. PIKfyve is associated with the cytosolic leaflet of early endosomes and its activity is required for endomembrane homeostasis, endolysosomal function and proper retrograde transport from the endosome to the trans-Golgi network. Introduction of a kinase dead mutant into cells induces a swollen vacuole phenotype that can be rescued by the injection of PI(3,5)P2. Inhibition of PIKfyve by pharmacological methods as well as RNAi also produces swollen vacuoles and disruption of endomembrane dynamics. It has been discovered that pharmacological disruption of PIKfyve with apilimod induces selective lethality of specific cancer cell lines through disruption of intracellular trafficking (see FIG. 2).

Example 3: Prediction of In Vivo Anti-Ebola Activity in Humans

Inhibition of cancer cell proliferation and inhibition of Ebola virus infection share a common mechanism i.e. inhibition of PIKfyve leading to vacuole formation and loss of intracellular trafficking. In the above clinical study, the trough TAEC values were greater than 25 mg/mL (60 nM). Since vacuole formation in cells at apilimod concentrations as low as 20 nM have been observed, one could conclude that oral administration of apilimod free base at doses ranging from 70 to 1000 mg/day should provide continuous PIKfyve inhibition to maintain vacuolization of cells and block Ebola infection in clinical therapy in patients.

Furthermore, it was shown in female Balb/c mice, a strain often used for in vivo Ebola infection studies, that constant infusion of apilimod as the bis-mesylate salt, using subcutaneously implanted osmotic mini-pumps (e.g. Alzet models 1007D, 15 mg/kg/day; model 2001, 30 mg/kg/day; vehicle: 25% DMSO, 25% Cremaphor, 50% sterile water) can provide sustained blood concentrations of apilimod in excess of 0.5 µM and 1 µM, respectively, as measured at 24 h (Table 1). Apilimod bis-mesylate was well tolerated under these conditions, with no visible adverse effects. In contrast, when apilimod was administered by intraperitoneal injection (30 mg/kg in 0.5%, methylcellulose in water) the blood concentration was below the level of quantitation at the 24 h time point.

Therefore, intravenous infusion of apilimod bis-mesylate to humans in an appropriate formulation (highly water soluble) at an appropriate rate, is expected provide potent Ebola virucidal activity and may be useful in the acute, critical care setting.

TABLE 1

Comparison of Apilimod plasma concentrations following I.P. injection, continuous S.C. Infusion, or both simultaneously in Balb/C mice

| Group | Route Pump (S.C.) | Route I.P. (injection) | Vehicle Pump (S.C.) | Vehicle I.P. (injection) | Dose (Bis-mesylate salt) Pump (S.C.) | Dose (Bis-mesylate salt) I.P. (injection) | Apilimod Ave. Plasma Conc. (µM) |
|---|---|---|---|---|---|---|---|
| 1 | ✓ | ✓ | DRW | MC | — | — | — |
| 2 | — | ✓ | — | MC | — | 30 mg/kg | BQL |
| 3 | ✓ | ✓ | DRW | MC | ~15 mg/kg/d | 30 mg/kg | 0.682 |
| 4 | ✓ | ✓ | DRW | MC | ~30 mg/kg/d | 30 mg/kg | 1.01 |
| 5 | ✓ | ✓ | DRW | DRD | — | 30 mg/kg | — |
| 6 | — | ✓ | — | DRD | — | 30 mg/kg | BQL |
| 7 | ✓ | ✓ | DRW | DRD | ~15 mg/kg/d | 30 mg/kg | 0.613 |
| 8 | ✓ | ✓ | DRW | DRD | ~30 mg/kg/d | 30 mg/kg | 1.76 |
| 9 | ✓ | — | DRW | — | ~15 mg/kg/d | — | 0.755 |
| 10 | ✓ | — | DRW | — | ~30 mg/kg/d | — | 1.87 |

The following study protocol was carried out to obtain the results discussed above:

Study Duration
  Dosing: Days 1 to 6, PK determination: Day 7
Formulations
  DRW: 25% DMSO, 25% Cremophor RH40, 50% Sterile water.
  MC: 0.5% methylcellulose in water.
  DRD: 10% DMSO, 13.5% Cremophor RH40, 76.5% 5% dextrose in water.
Alzet Mini-Pumps
  1007D Alzet pump used to dose ~15 mg/kg/d (Reservoir volume=100 µL)
  2001 Alzet pump used to dose ~30 mg/kg/d (Reservoir volume=200 µL)

Drug concentration is 25 mg/mL in both pumps
Dosing Volume
    10 mL/kg for I.P. injection
    0.5 µL/h for 1007D pump
    1.0 µL/h for 2001 pump
Dose Groups
    MC formulation with I.P. injection was used in mice in Groups 1 to 4.
    DRD formulation with I.P. injection was used in mice in Groups 5 to 8. DRW formulation was administered by Alzet mini-pump in all groups except 2 and 6. Group 1 and 5 are DRW formulation controls (i.e. no drug).
    All groups received I.P. drug or I.P. control except groups 9 and 10—the latter are the mini-pump infusion ONLY groups.
Conclusions
    1.) S.C. continuous mini-pump infusion of apilimod bismesylate, with (Groups 3 and 4, Groups 7 and 8) or without (Groups 9 and 10) concomitant I.P. injection, delivers therapeutically relevant steady state plasma concentrations of apilimod in Balb/c mice (based on Day 7 data).
    2.) Steady state plasma concentration is roughly proportional to infusion rate. Since the drug concentration is the same (25 mg/mL) for both infusion rates, steady state plasma concentration is roughly proportional to dose (Group 3 vs 4, Group 7 vs 8, Group 9 vs 10).
    3.) I.P. injection alone fails to provide measurable plasma concentration of apilimod 24 h after the final dose, irrespective of formulation (Groups 2 and 6).
    4.) S.C. continuous mini-pump infusion alone is sufficient to provide therapeutically relevant steady state plasma concentrations of apilimod.

Example 4: In Vitro Efficacy Against Ebola Proliferation

Figure 4A:
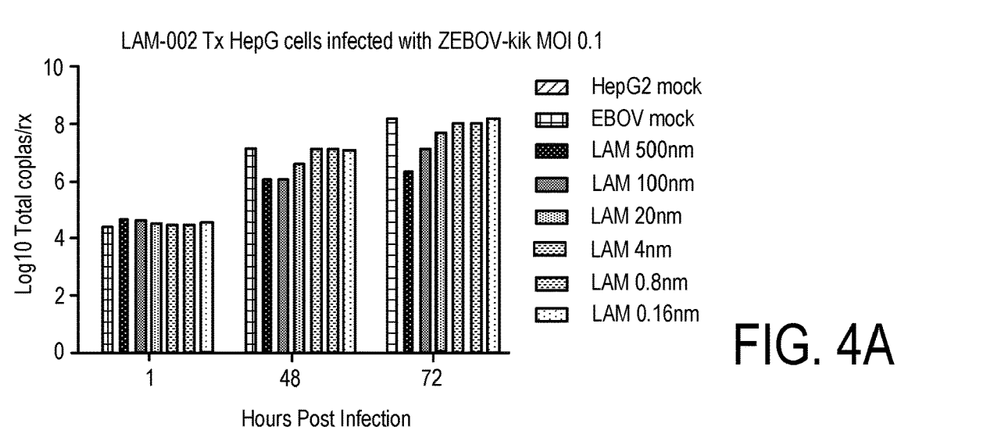
Figure 4B:
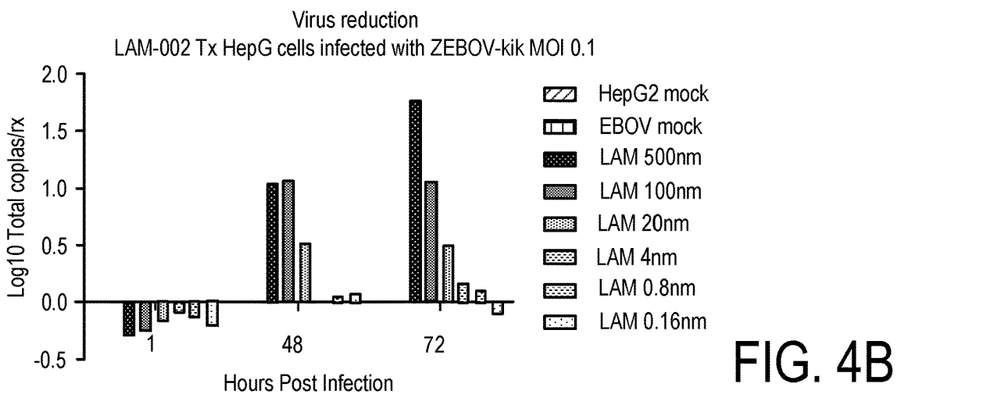
Figure 4C:
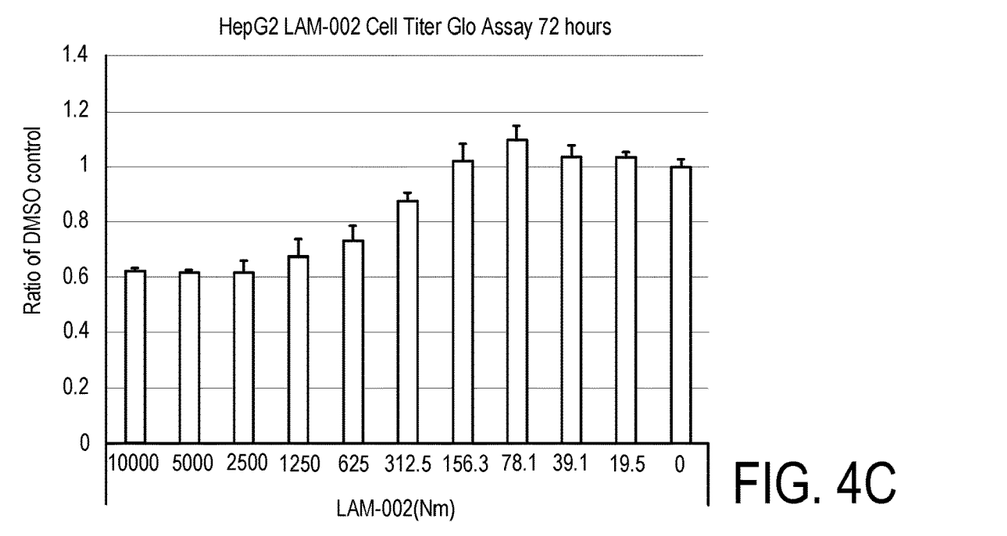

There are five species in the genus Ebolavirus: Zaire ebolavirus (ZEBOV), Sudan ebolavirus (SUDV), Reston ebolavirus (RESTV), Tai Forest ebolavirus (TAFV) and Bundibugyo ebolavirus (BDBV) (Olszanecki R, 2014). These EBOV species have been sequenced including the ZEBOV strain Kikwit, revealing RNA genome encodes genes for viral proteins: nucleoprotein (NP), glycoprotein, RNA dependent RNA polymerase (L) and matrix proteins (VP24, 68 VP30, VP35 and VP40). A number of the ZEBOV genes are used as surrogate markers of viral load and propagation. For the following in vitro study, the VP30 gene was used.
Methods
    HepG2 cells were infected at a multiplicity of infection (MOI) 0.1 with the virus ZEBOV-Kikwit, rocking every 15 minutes at 37 degrees Celsius for one hour. The inoculum was removed and cells washed 4 times with media and replaced with 10% FBS EMEM alone or 10% FBS EMEM with 6×5-fold dilutions of LAM-002 starting at 500 nanomolar (nM), e.g. 500, 100, 20, 4, 0.8, and 0.16. Samples for quantitative reverse transcription polymerase chain reaction (qRT-PCR) and plaque assay were collected at 48 and 72 hours post-infection.
    RNA was isolated from supernatants utilizing the Viral RNA mini-kit (Qiagen) using 100 µL of supernatant into 600 µL of buffer AVL. Primers/probe targeting the VP30 gene of EBOV were used for quantitative real-time PCR (qRT-PCR) with the probe used here being 6-carboxyfluorescein (6FAM)-5'CCG TCA ATC AAG GAG CGC CTC 3'-6 carboxytetramethylrhodamine (TAMRA) for the Kikwit in vitro studies (Life Technologies). EBOV RNA was detected using the CFX96 detection system (BioRad Laboratories) in One-step probe qRT-PCR kits (Qiagen) with the following cycle conditions: 50° C. for 10 minutes, 95° C. for 10 seconds, and 40 cycles of 95° C. for 10 seconds and 59° C. for 30 seconds. Threshold cycle (CT) values representing EBOV genomes were analyzed with CFX Manager Software, and data are shown as genome equivalents (GEq). To create the GEq standard, RNA from EBOV stocks was extracted and the number of EBOV genomes was calculated using Avogadro's number and the molecular weight of the EBOV genome.
    Virus titration was performed by plaque assay with Vero E6 cells from all supernatants. Briefly, increasing 10-fold dilutions of the samples were adsorbed to Vero E6 monolayers in duplicate wells (200 µL); the limit of detection was 25 pfu/mL.
Results
    Results of a representative experiment are shown in two formats in FIG. 1A and FIG. 1B. FIG. 4A shows a bar graph of the results of Log 10 total copies of virus per treatment (Rx) vs time-for the qRT-PCR on HepG2 cells for the time-points post-infection with ZEBOV-Kikwit: 1 hour, 48 hours and 72 hours. FIG. 4B shows bar graph of the FIG. 1A results Log 10 total copies reduced per Rx as compared to EBOV mock vs time. After one hour of treatment no change in ZEBOV concentration level. After 48 hours treatment with LAM-002 (apilimod dimesylate) at 20 nM, 100 nm, and 500 nM; the ZEBOV virus propagation was lowered by 0.5, 1.0 and 1.0 log 10 number of virus copies, respectively. After 72 hours of treatment with LAM-002 at 20 nM, 100 nm, and 500 nM; the ZEBOV virus propagation was again lowered by the values of 0.5, 1.0 and 2.0 log 10 number of virus copies, respectively.
    FIG. 4C shows the CellTiter-Glo Luminescent Cell Viability Assay of LAM-002 treatment of HepG2 cell line for 72 hours at concentration range of 10,000 nM to 19 nM at two fold dilutions, performed according to manufacturer's instructions (Promega). The viability of the HepG2 cells is greater than 73% at 625 nM, 87% at 325 nm, 100% at 156 nM and lower concentrations of LAM-002. The data of viability over range of LAM-002 verifies that the observations of lower virus levels were not due to decreased cell number or cell toxicity.
    The experimental data show a LAM-002 dose dependent decrease of ZEBOV levels and provide evidence of the in vitro efficacy of LAM-002 as a small molecule therapy to reduce Ebola virus propagation and viral load.

What is claimed is:

1. A method for inhibiting an Ebola or Marburg viral infection in a mammalian subject in need thereof, the method comprising administering to the mammalian subject a composition comprising an effective amount of apilimod, or a pharmaceutically acceptable salt thereof.

2. The method of claim 1, wherein the apilimod is apilimod free base or a pharmaceutically acceptable salt thereof.

3. The method of claim 1, wherein the mammalian subject is a human.

4. The method of claim 1, further comprising administering to the mammalian subject at least one additional antiviral agent, either in the same composition as the apilimod or a pharmaceutically acceptable salt thereof, or in a different composition.

5. The method of claim 4, wherein the anti-viral agent comprises an antibody or a combination of antibodies.

6. The method of claim 4, wherein the anti-viral agent comprises a small interfering RNA (siRNA) or a combination of siRNA molecules.

7. The method of claim 6, wherein the siRNA or combination of siRNA molecules targets one or more Ebola virus proteins.

8. The method of claim 7, wherein the siRNA or combination of siRNA molecules targets one or more Ebola virus proteins selected from the group consisting of the Zaire Ebola L polymerase, Zaire Ebola membrane-associated protein (VP24), and Zaire Ebola polymerase complex protein (VP35).

9. The method of claim 4, wherein the anti-viral agent is an interferon.

10. The method of claim 3, wherein the apilimod, or a pharmaceutically acceptable salt thereof is administered via an oral, intravenous, or subcutaneous route.

11. The method of claim 10, wherein the administration of the apilimod, or a pharmaceutically acceptable salt thereof is once daily, twice daily, or continuous for a period of time.

12. The method of claim 10, wherein the apilimod, or a pharmaceutically acceptable salt thereof is administered in an amount of 70 to 1000 mg/day.

13. The method of claim 2, wherein the pharmaceutically acceptable salt is selected from a sulfate, citrate, oxalate, chloride, bromide, iodide, nitrate, bisulfate, phosphate, acid, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate.

14. The method of claim 13, wherein the pharmaceutically acceptable salt is selected from the group consisting of a chloride, methanesulfonate, fumarate, lactate, maleate, pamoate, phosphate, and tartrate.

15. The method of claim 1, wherein the pharmaceutically acceptable salt is apilimod dimesylate.

16. The method of claim 15, wherein the amount of apilimod dimesylate is from 0.001 mg/kg to about 1000 mg/kg.

* * * * *